United States Patent [19]
Kell

[11] Patent Number: 6,124,136
[45] Date of Patent: Sep. 26, 2000

[54] METHOD OF MONITORING COMPLIANCE WITH METHADONE TREATMENT PROGRAM

[75] Inventor: Michael Kell, Atlanta, Ga.

[73] Assignee: U. D. Testing, Inc., Gainesville, Ga.

[21] Appl. No.: 08/145,821

[22] Filed: Nov. 2, 1993

[51] Int. Cl.⁷ .................................................. G01N 33/48
[52] U.S. Cl. ........................ 436/111; 436/816; 436/901
[58] Field of Search .................................. 436/111, 816, 436/901; 422/61

[56] References Cited

U.S. PATENT DOCUMENTS

| | | | |
|---|---|---|---|
| 2,564,247 | 8/1951 | Carson et al. | 23/230 |
| 3,856,469 | 12/1974 | Schneider et al. | 23/230 |
| 3,901,655 | 8/1975 | Shukla et al. | 23/230 |
| 4,104,367 | 8/1978 | Gomez et al. | 424/1 |
| 4,196,185 | 4/1980 | Focella et al. | 424/1 |
| 5,047,329 | 9/1991 | Suzuki | 435/18 |
| 5,137,692 | 8/1992 | Fritz | 422/61 |
| 5,179,027 | 1/1993 | Fisher | 436/56 |

OTHER PUBLICATIONS

Balabanova et al. "Methadone Distribution in Blood, Cerebrospinal Fluid, Urine and Organ Tissue", EMBASE No: 92091431.

Nilsson et al. "Effects of Urinary pH on the Disposition of Methadone in Man", EMBASE No: 82171209.

*Primary Examiner*—Lyle A. Alexander
*Attorney, Agent, or Firm*—Kennedy, Davis & Hodge LLP

[57] ABSTRACT

A method of monitoring compliance of a patient that has been placed on a methadone maintenance program by determining plasma methadone concentration from urine methadone concentration. An unadulterated urine sample is obtained from the patient. The urine methadone concentration, pH, and specific gravity are measured. The plasma methadone concentration is calculated as a function of urine methadone concentration, specific gravity, and pH. The calculated plasma methadone concentration is compared with an expected value for the maintenance program prescribed.

16 Claims, 5 Drawing Sheets

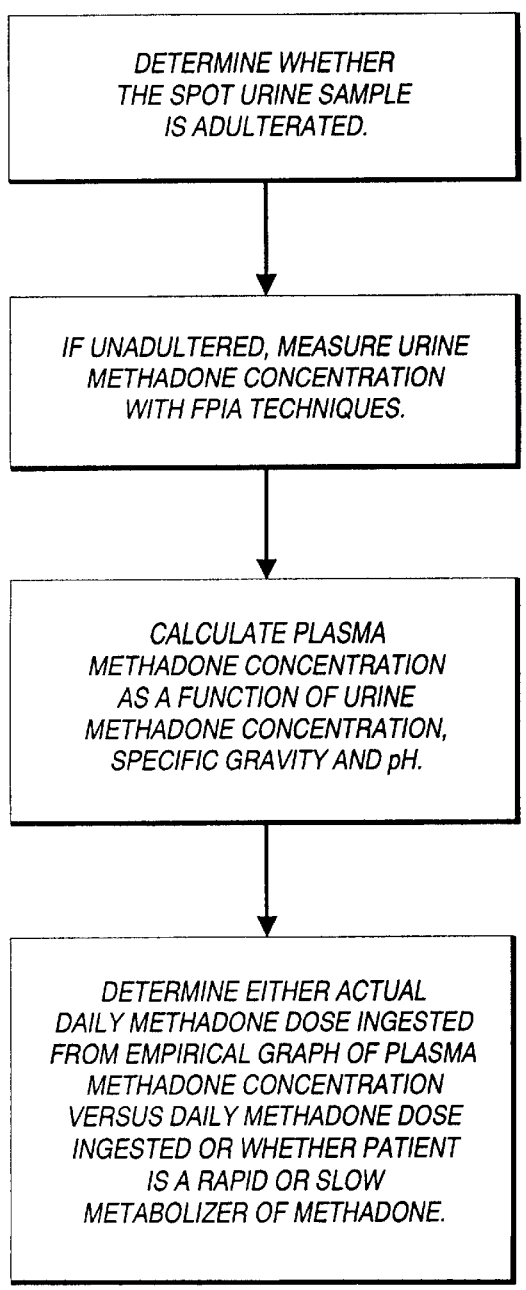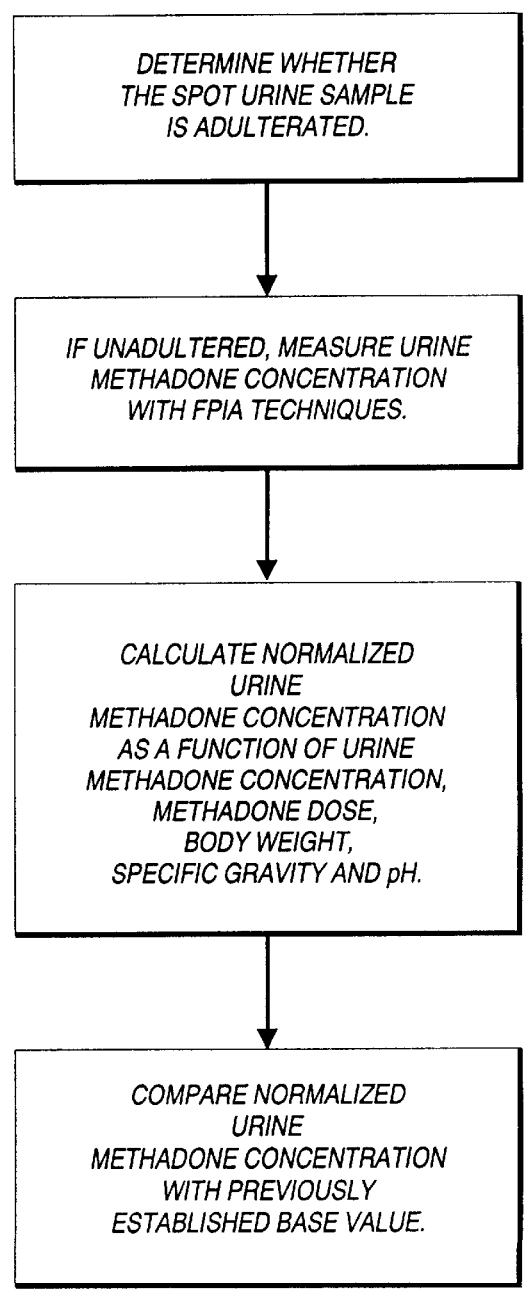

METHOD OF MONITORING COMPLIANCE WITH METHADONE TREATMENT PROGRAM

TECHNICAL FIELD

The present invention relates to therapeutic drug monitoring. More particularly, the invention relates to methods of monitoring the amounts of methadone ingested and resultant concentration levels in specific bio-fluids in patients placed on methadone treatment programs for compliance therewith either for treatment of a biochemical dependence upon opioid drugs and/or alleviation of suffering from opioid-responsive, chronic pain syndromes.

BACKGROUND OF THE INVENTION

Opioids are a class of alkaloids comprised of natural analogs, chemically-modified natural analogs and synthetic congeners which are biologically similar in action to endogenously produced mammalian neurohormones, the enkephalins and the endorphins; which are important for mood regulation, biochemical homeostasis and relief of pain. Opioids generally function by inhibiting or modifying nociceptive transmissions into and within the spinal cord and higher central nervous system, including the limbic structures of the brain; hence, alleviating pain and maintaining normal mood. Secondary effects, which generally are undesirable, but to which tolerance develops with continued use, consist of sedation, respiratory depression and euphoria.

Opioid alkaloids, be they natural analogs or synthetic congeners, are highly addictive compounds, that with repetitive use, can damage and permanently interfere with the proper functioning of an organism's neural, hormonal, immunological and biochemical processes. Opioids are generally derived from the opium poppy, Papaver somniferum, or are synthetically manufactured. Common opioids include: codeine, propoxyphene, meperidine, heroin, morphine, oxycodone, hydromorphone, hydrocodone and paregoric.

A majority of persons who become biochemically dependent upon opioids either through prescription or illegal use experience great difficulty eliminating their dependency upon such drugs. When independent efforts fail and abuse continues, an opioid or narcotics addict may enter into an extended rehabilitative treatment program designed to prevent continued drug use and the associated negative medical and social consequences; with methadone maintenance programs now being the most commonly employed and potentially the most efficacious treatment modality. Such patients are treated under specific requirements of the Federal Register 21 CFR Part 291, attending a clinic for observed ingestion of methadone once, twice, thrice or more times a week.

Another important and generally accepted use for methadone within the medical community is alleviation of severe, organically-based pain syndromes in persons with cancer, nerve injuries, musculoskeletal damage and so on.

Methadone is a synthetic opioid which: (1) prevents the occurrence of withdrawal symptoms and drug cravings that occur when use of other opioids is discontinued, (2) prevents euphoria and drug reward when other opioids are ingested, inhaled or injected and (3) alleviates nociceptive and neuropathic sensory input into the central nervous system by its actions as a potent, and nearly pure (no interfering metabolites), agonist for the mu-receptor subfamily of the larger family of opioid cell membrane binding/transduction sites. Moreover, methadone when given in properly prescribed doses, unlike other potent and short half-life opioids, has not been shown to cause permanent and detrimental changes in a patient's biochemistry; making it safe to prescribe for extended time frames.

Typically, both in standard methadone maintenance programs and in chronic pain clinics utilizing methadone, physicians combine psychotherapy, psychosocial counseling, medical care and qualitative urine drug screening with prescribed daily doses of methadone to reduce illicit (illegal and/or not medically approved) opioid use.

Although illicit opioid use tends to decrease as methadone dose increases, a significant percentage of patients continue to abuse opioids even though apparently maintained on high methadone doses. Continued use of opioids by these patients may be attributed to several factors: (1) poor bioavailability and/or rapid hepatic metabolism of methadone resulting in plasma and blood methadone levels too low for alleviating the signs and symptoms of opioid withdrawal, blocking the euphorogenic effects of other opioids and normalizing mood, (2) diversion of methadone by patients not attending a clinic every day to illicit use by other addicts and (3) ingestion of non-opioid drugs such as barbiturates and anticonvulsants that counter the effect of methadone.

Monitoring of patients in methadone maintenance programs, including those dealing with chronic pain patients, aids physicians in effectively adjusting the prescribed methadone dose and in assuring patient compliance with their prescribed dose and medical treatment. Current methods commonly utilized for monitoring patients enrolled in methadone maintenance treatment programs are clinical observation for opioid intoxication or withdrawal; and less frequently, scheduled or random, repetitive, qualitative urine drug screening for uncovering illicit opioid use and insuring that methadone is indeed contained within the urine sample. Occasionally, research centers may directly measure a patient's plasma methadone concentration by obtaining a blood sample from the patient.

Clinical observation involves individual counseling and close personal supervision by physicians for evaluating the effects of a patient's methadone dose and observing signs of opioid intoxication or withdrawal. Physicians observe physiological signs and symptoms, listen to patient complaints and degree of pain relief, and evaluate psychological changes over time. This method is time consuming, expensive and highly subjective.

To supplement clinical evaluations, physicians also commonly monitor suspected illicit opioid use and ingestion of methadone by qualitatively analyzing urine for opioid-like and methadone-like immunoreactivity. A standard laboratory procedure used for this is enzyme-multiplied immunoassay technique or EMIT. Utilizing an arbitrary cutoff value, this method provides the clinician with only a simple positive or negative indication of the possible presence or absence of opioids and methadone in a patient's urine. It does not provide information concerning the time or amount of last drug use or whether or not the prescribed dose of methadone was ingested properly, diverted or supplemented.

Currently, utilizing only clinical evaluation and/or qualitative urine drug screening test results, physicians attempt to assess the condition of each patient and adjust methadone dose accordingly. For example, if a patient is continually testing positive for opioids or complains of continuing subjective opioid withdrawal symptoms, a physician may conclude that the currently prescribed dose of methadone is not sufficient to curb the body's desire for opioids and may increase the prescribed dosage. This highly subjective monitoring method can result in over-medication, patients being given more methadone than they require, creating an unnecessary reliance on methadone. Alternately, physicians sometimes conclude, erroneously, that a patient's methadone dose should be sufficient to prevent opioid withdrawal and drug cravings and deny the patient a further increase sufficient to stop illicit opioid use. Such action can expose the patient to further intravenous drug use and the associated negative medical and social consequences which can follow—HIV, hepatitis, blood poisoning and so on.

To eliminate illicit opioid use, analytical studies using venous blood samples obtained from stable patients have shown that plasma methadone concentrations ranging from 150–600 ng/ml are necessary. Unfortunately, measurement of plasma methadone concentration requires the use of time consuming, expensive, and highly technical analytical procedures such as high pressure liquid chromatography and gas chromatograph/mass spectrometry. Additionally, for many patients obtaining plasma samples is invasive, offensive and difficult due to inadequate venous access. Medical professionals must also be concerned about their own health safety in doing this since they are exposed to blood products from a patient group with high prevalence to hepatitis and HIV infection. Therefore, such procedures are conducted only in research centers and are not generally utilized in standard methadone maintenance programs.

The methods described above, while providing some useful information relative to patient opioid use and treatment compliance, have distinct drawbacks which limit their usefulness in daily application for methadone maintenance programs. Therefore, it is seen that a need remains for a better method of monitoring opioid addicted patients who have been placed on methadone maintenance programs for compliance therewith. It is to the provision of such that the present invention is primarily directed.

SUMMARY OF THE INVENTION

In accordance with the present invention, a patient's urine, rather than blood or plasma, is analyzed for methadone concentration as an indicator of plasma methadone concentration which in turn provides a correlation to methadone dose ingested. This information may be used to monitor the patient's compliance with a prescribed methadone program. It also can be used to establish the proper methadone dose.

A patient is initially prescribed a methadone dose based on several factors including the severity and duration of opioid addiction, amount of opioid previously used, dependence upon other non-opioid drugs, previous medical history, patient sex, pregnancy status, patient weight and ingestion of other therapeutic medications. Normally methadone dose is adjusted upwardly until a patient no longer complains of withdrawal signs and symptoms and loses his or her desire to use illicit opioids. Generally, attaining 24-hour trough plasma methadone concentrations between 150–600 ng/ml, which are generally recognized in past studies as most effective in deterring illicit opioid use, are desirable.

As methadone dose is increased, usually 10–20 mg every few days, the patient's 24-hour trough plasma methadone concentration, as calculated by the present invention, is compared to previously measured plasma methadone concentrations; helping the physician determine both how the patient is metabolizing methadone and what the most likely final methadone dose will be. Over time, a unique plasma concentration-daily methadone dose relationship is derived for each individual patient, which can be compared to the relationship expected for that particular patient or for an average patient. If the two relationships are not similar, the patient's metabolism rate may account for any over- or under-effectiveness of the prescribed dose. A physician, in accounting for the patient's individual metabolism rate, can now optimize the patient's methadone dose to achieve an efficacious and safe plasma methadone concentration. Further, once the optimum methadone dose is established for the patient, a physician can monitor the patient for compliance with his or her prescribed dose by comparing the plasma methadone concentration of methadone, as calculated by the present method, with his expected, historical plasma methadone concentration for that particular methadone dose; hence, uncovering covert methadone diversion or supplementing.

Briefly described, the method of determining plasma methadone concentration from urine comprises the step of first determining whether the urine sample is indeed from the patient in question and whether or not it is adulterated. This can be done by comparing urine pH, specific gravity, and creatinine level with that of normal urine and specific values previously determined for the patient. If found to be unadulterated and probably from the patient in question, the urine methadone concentration is measured with standard quantitative laboratory methods, such as high pressure liquid chromatography or gas chromatography/mass spectrophotometry (GC/MS). Preferably, because of the ease and rapidity of analysis, florescence polarization immunoassay (FPIA) is employed such as with an Abbott TDX or ADX Analyzer.

Once an analytical value has been determined for the actual concentration of methadone in the sample, adjustments are made to account for the effects of variations in certain urinary parameters upon this concentration. A relationship exists between the actual concentration of methadone adjusted for compounding effects of urine specific gravity, the renal clearance of methadone as a function of urine pH, and the concurrent plasma methadone concentration. By obtaining multiple urine samples from a patient, once or twice a week, it is possible to establish a stable, baseline, 24-hour trough plasma methadone concentration for each patient against which a current or future value can be statistically compared.

Finally, given a patient's weight an estimate of the final daily methadone dose required by a patient can be determined. A previously developed empirical graph of plasma methadone concentration (ng/ml) versus daily oral methadone dose ingestion (mg/day) for the general population is utilized. This curve represents the 24 hour trough plasma methadone concentration expected for the average patient comprising the cohort from which the data were generated. For example, an average patient having a weight of 154 pounds (70 Kg) and an average methadone plasma half-life of 31.5±10.2 hours, normally ingesting methadone every 24 hours (approximate range 18–30 hours), and providing a second or later urine void of the day. In the event a particular patient falls outside the "average profile", it is a simple matter to adjust for these parameters in relating the patient's actual plasma methadone level to his average daily ingestion of methadone.

The actual urine methadone concentration may also be converted to a urinary parameter-normalized urine methadone concentration which is a constant and individual value for each patient. The calculation incorporates the measured actual urine methadone concentration, methadone dose, patient's weight, urine pH, and urine specific gravity. By establishing an individual's base value for the urinary parameter-normalized urine methadone concentration, subsequent readings may be compared with the base value to evaluate whether the patient is compliant with his or her prescribed dose.

Again, this is done by first determining whether the urine sample is adulterated as by comparing urine pH, specific gravity and creatinine level with that of normal urine and previously established patient baseline values. If not adulterated, the actual urine methadone concentration is measured as previously described. The urinary parameter-normalized urine methadone concentration is next calculated as a function of the urine methadone concentration, methadone dose, patient's weight, urine specific gravity, and urine pH. Finally, a comparison of this value is made with a previously established individual's base value for urinary parameter-normalized urine methadone concentration.

BRIEF DESCRIPTION OF THE DRAWINGS

FIG. 1 is a block diagram of a preferred method of the present invention, the last step being optional.

FIG. 2 is a block diagram of another preferred method of the present invention.

DETAILED DESCRIPTION OF THE INVENTION

Testing for Adulteration

Figure 3:
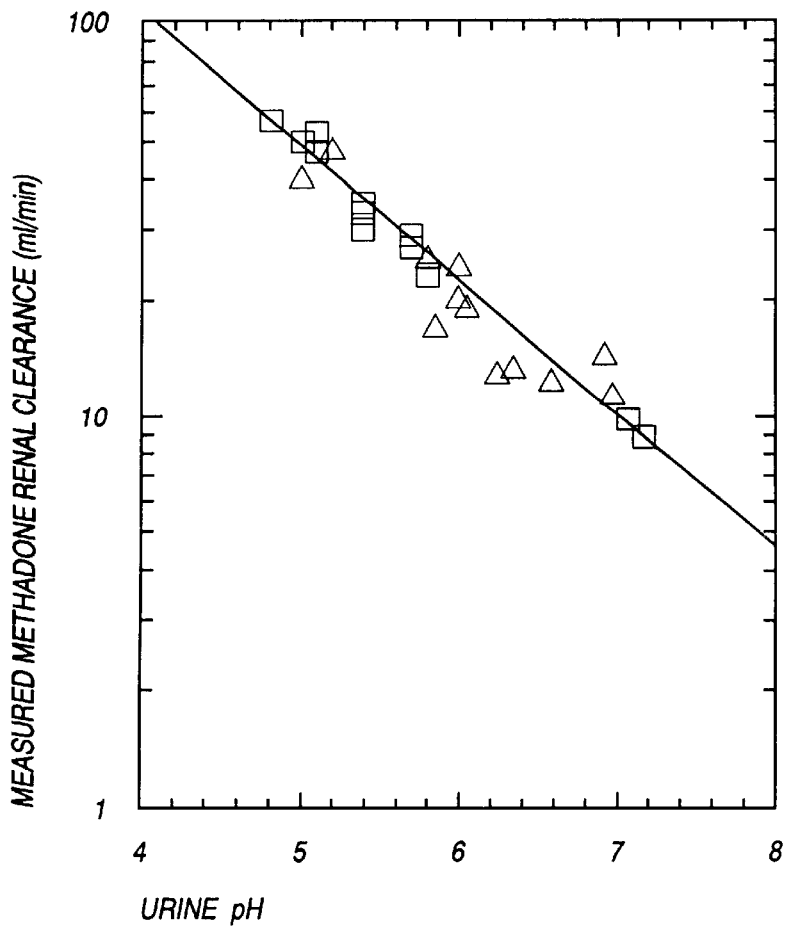
FIG. 3 is a graph of renal methadone clearance versus urine pH.

First, a supervised, spot sample of urine is collected from a patient. Several properties of the urine are measured to evaluate whether the urine is adulterated, adulteration being the altering by a patient of his or her urine in an effort to prevent detection of illicit drug use or diversion of methadone. Adulteration typically is accomplished by adding foreign substances to the urine such as salt, bleach, or vinegar. Many patients attempt to dilute amount of drugs in the urine sample by drinking large quantities of water or by adding water to the sample. Adulteration may also occur by substituting another person's urine for the patient's own urine, including instillation of foreign urine into the patient's bladder.

In checking for adulteration, urine pH is measured, as with the use of a pH Data Logger type meter available from Oakton, to see if it is within the normally expected pH range of 4.5 to 8.5. Urine specific gravity (sg) is also measured to see if it is within the normal range of 1.004 to 1.035 units; a Digital Urinometer by Biovation may be used for this test. Creatinine, an end product of glycine and arginine metabolism excreted through the kidneys, is measured to evaluate renal function. The creatinine level in human urine usually ranges from 8 to 500 mg/dl, the range being affected by variables such as age, sex, diet, lifestyle and geographic location. Creatinine levels generally are homeostatically maintained by the body at a constant value for each individual patient over his or her lifetime. Creatinine levels may be determined on many different analyzers, including a TDx REA Creatinine System available from Abbott Laboratories. All of these tests are helpful in establishing normally expected ranges for each patient and the overall population of patients.

Once pH, specific gravity, and creatinine level values for the spot urine sample are obtained for a particular patient, comparisons can be made between the sample in question and values previously measured (if already available) both for the patient and for normals to ascertain whether the urine sample is adulterated. If no adulteration is found, a data base is created or extended for the patient so that a basis of comparison exists for future spot urine samples. Of the three measures, urinary creatinine level is generally the most useful indicator as to whether the spot sample is that of the patient or of someone else.

Determination of Raw Urine Methadone Concentration

The unadulterated sample is next analyzed for methadone concentration, preferably using Fluorescence Polarization Immunoassay (FPIA) technology. In this regard an Abbott TDX or ADX Analyzer may be profitably employed. Other standard analytical methods could also be used such as chromatography or other types of immunoassay. The value obtained is the raw urine methadone concentration of the patient, u.

Determination of Plasma Methadone Concentration

Plasma methadone concentration is obtained from the raw urine methadone concentration by utilizing a standard dimensionally correct relationship known as the renal clearance, which is, $$cl = (u \cdot v)/p \qquad (1)$$

where cl is renal clearance (ml/min), u is raw urine methadone concentration (ng/ml), v is the volume of urine collected in time (ml/min) or otherwise known as the urine volume production rate, and p is the measured plasma methadone concentration at the midpoint of the collection period (ng/ml).

Since the actual, current renal methadone clearance is not generally known for any one patient, nor can it easily be directly measured under normal clinic conditions, it must be estimated from an empirical relationship. It has now been found from actual experiments measuring urine and plasma methadone concentrations over timed collection periods (which recognizes that the renal clearance for methadone is strongly affected by urinary pH because of the weakly basic properties of methadone), that renal clearance relates to urine pH in the range 4.8–8.7 (see FIG. 3) as, $$cl = 104{,}218 \cdot pH^{(-4.76)} \qquad (2)$$

and for which generally, a strong dependence upon actual patient weight is not noticed.

Rearranging Equation (1), the plasma concentration of urine may be calculated as follows, $$p = u \cdot v / cl \qquad (3)$$

The actual, raw urine methadone concentration is known from the FPIA results. Renal clearance can be calculated from Equation (2) by utilizing the urine pH previously measured in testing for adulteration. However, actual values of the urine volume production rate, v, are not available since routine clinical urine sampling procedures only provide a point-in-time or spot urine sample.

Persons skilled in the art state that it is not possible to calculate the plasma concentration of a drug from the spot urine sample; instead, a timed urine collection must be done (usually 24 hours). It has been found that these teachings are flawed and not grounded in fact.

It is now noted that renal excretion rates (mg/min) for drugs and urine metabolites are relatively constant for any patient during a typical day. This constancy has now been experimentally verified by looking at the renal excretion rates of methadone, benzodiazepines, other drugs and creatinine and other endogenous metabolites as a function of urine volume production rate. For example, using 12 compliant control subjects we have collected sequential, complete and timed (1–8 hours holding periods) aliquots of urine over 24 to 72 hour periods. For each and every urine aliquot, urine volume production rate (ml/min), specific gravity and creatinine concentration (ng/ml) were determined.

Using this data, a dimensionless, linear relationship was found to exist, which is the same for each and every patient, between a urine volume production rate factor (UVPRF) and a reverse urine creatinine excretion factor (RUCEF). For each individual, control, urine collection period, the UVPRF is defined by the ratio of urine volume production rate for each urine aliquot collected, v, to the urine volume production rate for the most concentrated sample in the collection period with a specific gravity usually near 1.030, v', $$\text{UVPRF} = v/v'. \quad (4)$$

The RUCEF factor is defined by the ratio of the creatinine concentration of the most concentrated urine aliquot with a specific gravity usually near 1.030, u', to the creatinine concentration for each urine aliquot collected, u, $$\text{RUCEF} = u'/u. \quad (5)$$

Figure 4:
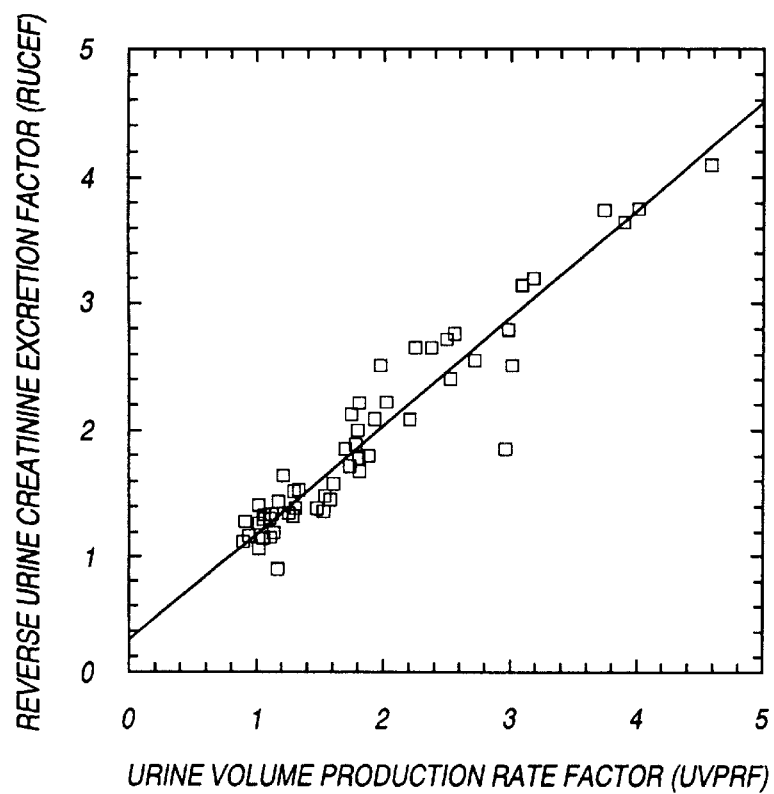
FIG. 4 is a graph of Reverse Urine Creatinine Excretion Factor versus Urine Volume Production Rate Factor.

This linear relationship is shown in FIG. 4. The best fit linear regression line is given by the expression, $$\text{RUCEF} = 0.942(\text{SE } 0.013) \cdot \text{UVPRF} + 0.121(\text{SE } 0.043) \quad (6)$$

$$u'/u = 0.942 \cdot v/v' + 0.121 \quad (7)$$

adjusted squared multiple R=0.985, standard error (SE) of estimate=0.242, F-ratio 4965.

Therefore, contrary to the traditional teachings of those skilled in the art, urine drug and metabolite concentrations, u, are inversely related to the volume of urine produced by the kidneys, v, clearly demonstrating that the product (u·v) is constant at any particular time point and urine pH (given a steady-state plasma methadone concentration p and renal clearance cl).

Since p, cl, and (u·v) at any time point and urine pH are constant, steady-state values, it follows that from Equation (7) some empirical mathematical relationship must exist between u and v such that given an arbitrary urine volume production rate v' and an equivalent u' at a reference point (specific gravity 1.030):

$$\{u \cdot v\}_{sg\ actual} = \{u' \cdot v'\}_{sg\ 1.030} \quad (8)$$

or upon rearrangement for u' gives, $$u' = u \cdot (v/v') \quad (9)$$

where the products given in Equation (9) are those measured for a spot urine collected with an actual specific gravity and a corrected specific gravity typical of a morning void of 1.030.

Figure 5:
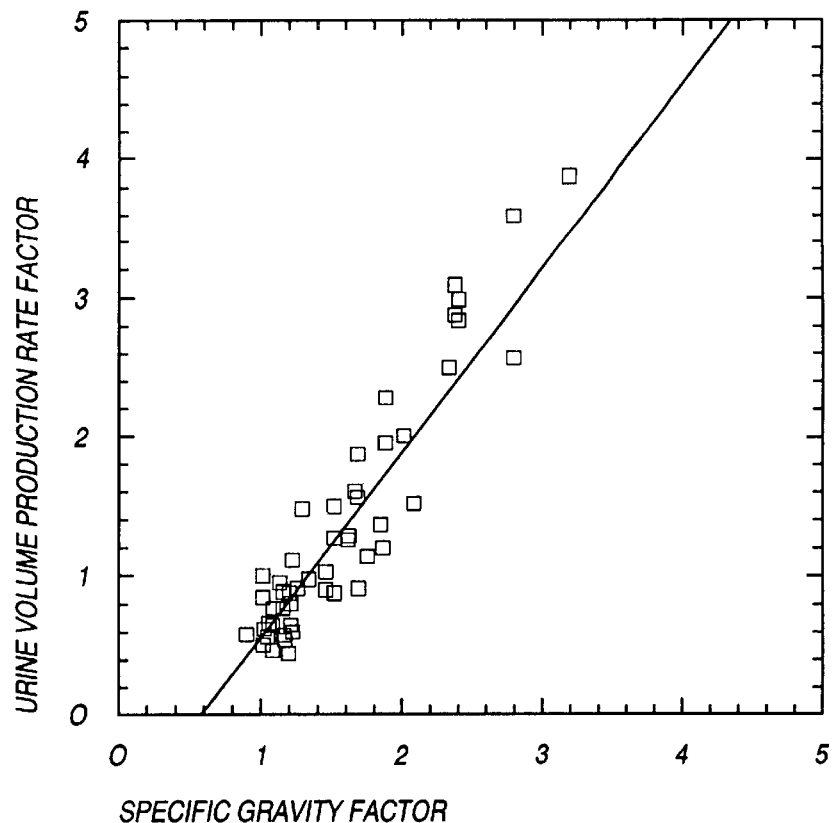
FIG. 5 is a graph of Urine Volume Production Rate Factor versus Specific Gravity Factor.

Using controlled urine collections, we have measured a urine volume production rate v' of 0.44 ml/min for persons with reasonably normal renal functions at a specific gravity of 1.030. It has also been discovered that a linear relationship exists between the urine volume production rate factor and the specific gravity factor (SGF), {(1.030–1.000)/(sg–1.000)}, as shown in FIG. 5 and given below:

$$\text{UVPRF} = v/v' = 2.43(\text{SE } 0.106) \cdot \text{SGF} - 1.43(\text{SE } 0.216) \quad (10)$$

where the adjusted squared multiple R=0.856, standard error of the estimate=0.787, F-ratio 482.

Combining all of the above considerations, plasma methadone concentrations can be calculated by substituting Equations (2, 8, 9 and 10) in Equation (3):

$$p = u \cdot v / cl \quad (11)$$
$$= u' \cdot v' / cl$$
$$= v' \cdot u \cdot (v/v') / cl$$
$$= 0.44 \cdot u \cdot (2.43 \cdot SGF - 1.43) / 104,218 \cdot pH^{(-4.76)}$$

where values of u, specific gravity, and pH are known from previous test results on a patient's spot urine sample.

Figure 6:
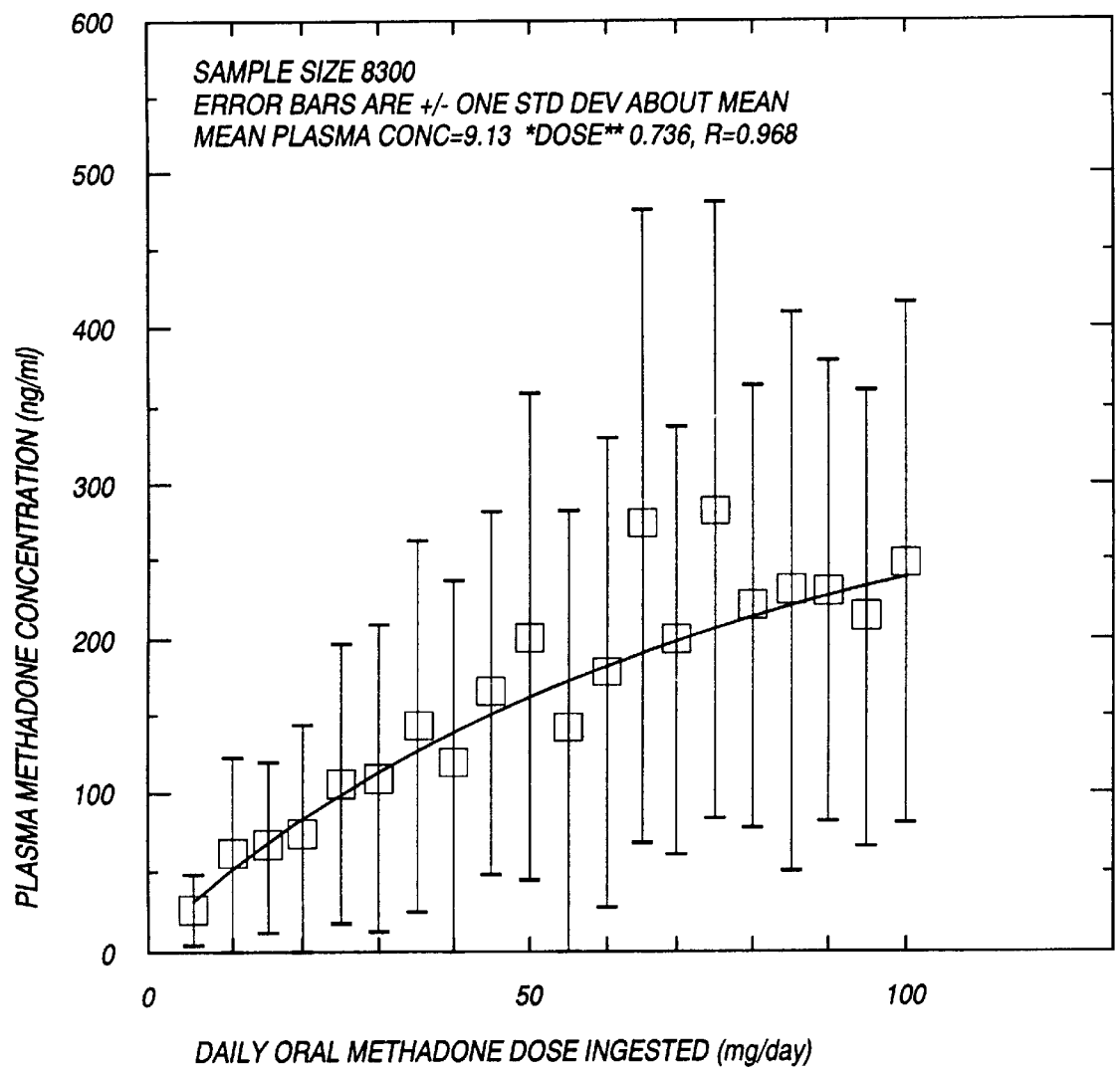
FIG. 6 is a graph of plasma methadone concentration versus daily oral methadone dose.

Comparing Patient's Calculated Plasma Methadone Concentration to that of an Average Patient for the Same Dose Once the plasma methadone concentration is calculated from Equation (11), it is compared with the plasma methadone concentration expected from an average patient on a similar daily methadone dose as shown in FIG. 6, which demonstrates how plasma methadone concentration varies with dose for the standard population. FIG. 6 was developed by utilizing data from 8300 urine samples from 150 methadone maintenance patients on controlled daily methadone dosages.

Using this figure, a clinician can estimate how a prescribed dose will effect a patient's methadone plasma level. For example, a patient on a 70 mg/day methadone dose is expected from FIG. 6 to have a plasma methadone concentration of 200 ng/ml. However, from the spot urine sample the calculated plasma methadone concentration is 100 ng/ml thereby indicating that the patient's body is quickly metabolizing the methadone and a higher dose is needed, that the patient is diverting the methadone to others or that the patient is simply not using it. Higher concentrations per dose suggest the opposite of the above. Knowing that the plasma methadone concentration does not correlate to the prescribed methadone dosage, the clinician now has valuable information to evaluate the next step in the patient's program.

An optional use of the calculated plasma methadone concentration is to estimate the methadone dose that the patient has taken. FIG. 6 is used to estimate the patient's methadone dose by adjusting the calculated plasma methadone concentration relative to any parameters of the patient that fall outside the average patient parameters, such as patient body weight, methadone plasma half-life, and time of ingesting dose.

Verification

In order to ascertain the effectiveness of the plasma methadone concentration formulation, blood and urine samples were taken from a control group of patients. Urine and blood samples were simultaneously analyzed for plasma methadone concentration using FPIA and GC/MS. The urine methadone concentration was converted to a calculated plasma methadone concentration utilizing the formulation of the present invention in Equation (11).

Figure 7:
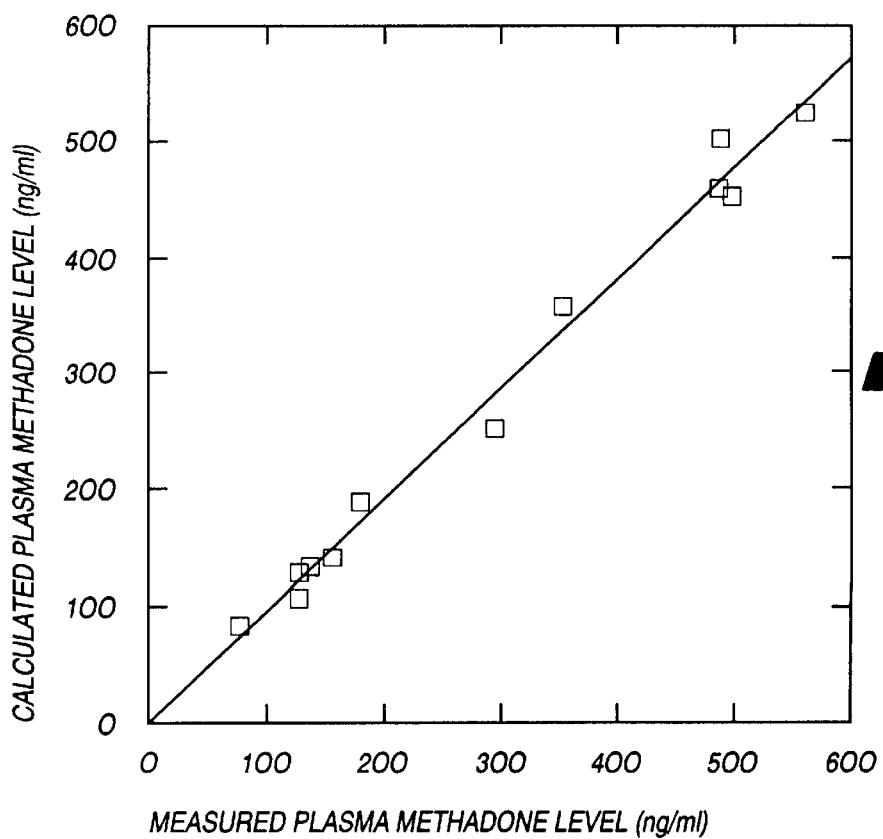
FIG. 7 is a graph of plasma methadone concentration calculated using the method of the present invention versus measured plasma methadone concentration using Abbott FPIA.

Referring now to FIG. 7, the accuracy of calculating plasma methadone concentration from urine methadone concentration is verified by the excellent linear agreement between the plasma concentrations calculated by the present method from random, spot urine measurements and concurrently measured plasma methadone concentrations using actual blood samples: Estimated=0.970(SE 0.034) ·Measured −1.25(SE 11.495), adjusted squared multiple R=0.987, standard error of estimate=20.155, F-ratio 810.

Determination of Urinary Parameter-Normalized Urine Methadone Concentration

The parameters of a patient's urine, such as pH and specific gravity, vary from one day to the next dependant upon the type and quantities of foods and beverages ingested. Additionally, individuals metabolizes these substances, as well as methadone, at different rates. To account for these variations, a urinary parameter-normalized urine methadone concentration, nu, is calculated that adjusts measured raw urine methadone concentration, u, in accordance with a prescribed methadone dose, urine specific gravity, patient's current body weight (lbs) and urine pH. The relationship between u, pH, dose and specific gravity was empirically developed using nonlinear regression analysis. Results were normalized to a dose level of 80 mg/day, a patient weight of 154 pounds, and urine pH of 6.5 giving the final equation for monitoring a patient's nu:

$$nu = \{(80/DOSE)^{0.823}\} \cdot \{(6.5/pH)^{-4.838}\} \cdot (WGT/154) \cdot UVPRF \cdot u \quad (12)$$

The urinary parameter-normalized urine methadone concentration is statistically constant and unique for each patient regardless of an individual's methadone metabolism and daily changes in urine parameters. Thus, a patient's baseline nu, once established accurately for an individual patient within a statistical margin of error, may be used to evaluate methadone diversion or supplementation in patients by comparing subsequent calculations of this value with the patient's particular established baseline. If the subsequent calculation is similar to the established baseline, the patient is complying with his prescribed dose.

The generation of a patient's nu baseline value is done using standard statistical techniques developed for relating the mean and standard deviation observed from a particular sampling distribution (of size n elements) to the mean and standard deviation expected for the whole population of values, both for each patient and the population of all patients. For further details one can refer to the text, Hahn GJ, Meeker WQ, Statistical Intervals, John Wiley and Sons, 1991.

To utilize such techniques it is first necessary to determine what the expected standard deviation is for the whole population of compliant patients under observation. Previously, it had been observed that although means value for nu are different for each patient, the observed variability about the mean for compliant patients is quite consistent and similar to the overall cohort of compliant patients; suggesting that the following statistical technique may be utilized.

Sequential, urine data was retrieved from computer files for 216 patients (13,000 data points) and transferred into a commercial statistical/graphical package produced by Systat, Inc. Each patient's data was sorted individually by ascending concentration for initial data review. All data points having unusual creatinine values <10 or >500 mg/dl or a methadone concentration <300 or >60,000 ng/ml were discarded as being suspect and non-physiologic. Additional outliers were eliminated from each patient file using manual review (preliminary statistic data were available as a guide). For statistical reasons, all patients having less than 10 acceptable data points were also eliminated.

Using the remaining data sets for each patient (180 persons, approximately 12,000 individual urine values), individual nu values were obtained from which individual means and standard deviations were calculated (method shown later).

Utilizing this data, a plot of sample size (for each patient) versus calculated sample standard deviation (for each patient) was generated. Approximately, 180 individual, standard deviations (y-axis) were plotted against samples sizes ranging from 10 to 200 (x-axis). Using standard 95% confidence limit tables from Hahn and Meeker, lower and upper limits were co-plotted on the above curve by adjusting the overall population standard deviation until the data bounded by the prediction curves enclosed all acceptable data. The average population standard deviation for the set of acceptably, compliant patients was found to be about 3000 for this particular set of patients, though it could be lower if further restrictions to the initial data set were applied.

Given this value, another set of prediction equations specifying the allowable range for the next measured nu for a particular patient, given a sample size of n, a mean nu for an individual patient and either the patient standard deviation or the population standard deviation (whichever is least), can be calculated as shown in Hahn and Meeker. If the measured value is within the acceptable statistical range, given a previously calculated mean and standard deviation, then it is accepted. If the value is too high or too low, this is marked on the urine drug screen under the column called Pred as shown in clinical cases #'s 4 and 5.

An alternative method which can be used to establish outliers for each patient data set, though less rigorous than the statistical method, is simply to specify a + and − range about the mean, say +/− 50% of an individual patient's mean. This simple method can give satisfactory and reasonable results.

Verification

Shown in Table 1 is a partial representation of data from a standard computer printout for a compliant patient in which is summarized both urine parameters and methadone concentrations. The last column in the figure represents the urinary parameter-normalized urine methadone concentration values for the patient which are quite constant once sg, pH, dose corrections are made to the raw urine methadone concentration.

TABLE 1

| Date | Dose | Temp | pH | SG | CR | u | p | nu |
|---|---|---|---|---|---|---|---|---|
| 04-20-92M | 70 | 98.0 | 5.40 | 1.022 | 335 | 6838 | 167 | 6966 |
| 04-15-92W | 70 | 96.0 | 5.70 | 1.024 | 268 | 6536 | 176 | 7381 |
| 04-13-92M | 70 | 96.0 | 5.90 | 1.019 | 271 | 5462 | 259 | 10913 |
| 04-10-92F | 70 | 98.0 | 5.70 | 1.021 | 377H | 5180 | 177 | 7430 |
| 04-06-92M | 70 | 98.0 | 5.90 | 1.028 | 261 | 7398 | 171 | 7208 |
| 04-02-92h | 70 | 96.0 | 5.70 | 1.026 | 271 | 5990 | 149 | 6254 |
| 03-30-92M | 70 | 94.0 | 5.60 | 1.021 | 303 | 4203 | 132 | 5532 |
| 03-25-92W | 70 | 98.0 | 5.20 | 1.021 | 271 | 8469 | 187 | 7790 |
| 03-24-92T | 70 | 98.0 | 6.00 | 1.023 | 243 | 3736 | 139 | 5852 |
| 03-20-92F | 70 | 96.0 | 5.80 | 1.024 | 272 | 5601 | 164 | 6881 |
| 03-16-92M | 60 | 94.0 | 5.30 | 1.022 | 286 | 7049 | 157 | 7448 |
| 03-13-92F | 60 | 96.0 | 5.70 | 1.019 | 277 | 4935 | 199 | 9473 |
| Mean: | | | | | 286 | 5950 | 173 | 7427 |
| SD: | | | | | 37 | 1372 | 33 | 1492 |
| CV: | | | | | 12.7 | 23 | 19.1 | 20 |
| Tests: | | | | | 12 | 12 | 12 | 12 |

Clinical Examples

Case #1: J. S. is a 52 year old woman with right-sided, migraine with aura headaches beginning after her hysterectomy at age 44 and prior to regular use of any medication. Her migraines begin with flashes of light and blurry vision in either eye. Often "a film covers my right eye." Prodromata are usually followed by right retro-orbital pain accompanied by photophobia and nausea. This patient also suffers tension headaches and headaches secondary to allergic rhinitis. She is able to clinically differentiate migraine and tension components of her headaches, as the migraine component is refractory to multiple trials of ergot alkaloids, benzodiazepines, NSAIDs, beta-blockers, calcium channel blockers and psychotherapy. Multiple CT scans have been normal.

J.S. had been biochemically dependent upon prescription opioids to relieve migraine pain for over a year prior to her referral to a methadone maintenance clinic. According to Federal Register 21 CFR Part 291, a person biochemically dependent (this is the current definition for opioid dependency utilized by the federal government) to narcotics for more than a year qualifies to enter into a methadone maintenance program.

J.S.'s situation is similar to that of approximately 0.5% of the general, adult population of the United States who are also biochemically dependent upon opioid medications because of legitimate medical illness and disease. Oftentimes, it is difficult for the clinician to determine whether or not the patient is currently using opioids for relief from organic pain or is treating the psychological sequelae of their disability. In either case, methadone maintenance is the most efficacious choice to help and protect the patient.

J.S. enrolled in the methadone maintenance program 36 months ago for pain management. Gradual titration to 35 mg of methadone was achieved over a short time period during which migraines slowly decayed in frequency and severity. During her time in treatment she has subsequently suffered only 2 migraine attacks which were greatly reduced in intensity. Both attacks were related to a transient decrease in plasma methadone levels below 80 ng/ml secondary to vomiting associated with viral syndromes.

A typical urine history is shown in Table 2 for this patient showing both estimated plasma methadone levels and the urinary parameter-normalized methadone concentration.

TABLE 2

| Date | Dose | Temp | pH | SG | CR | u | p | nu |
|---|---|---|---|---|---|---|---|---|
| 07-01-93h | 45 | 94.0 | 7.70 | 1.012 | 319 | 1069 | 348 | 21153 |
| 06-21-93M | 45 | 94.0 | 6.90 | 1.008 | 265 | 1336 | 426 | 25720 |
| 06-14-93M | 45 | 94.0 | 6.60 | 1.011 | 273 | 2109 | 368 | 22145 |
| 06-07-93M | 45 | 95.0 | 7.30 | 1.011 | 270 | 1883 | 532 | 32208 |
| 06-03-93h | 45 | 98.0 | 7.00 | 1.010 | 254 | 646 | 168 | 10174 |
| 05-27-93h | 45 | 94.0 | 7.60 | 1.018 | 269 | 1246 | 215 | 13051 |
| 05-20-93h | 45 | 95.0 | 6.80 | 1.011 | 275 | 1285 | 259 | 1558S |
| 05-13-93h | 45 | 95.0 | 7.80 | 1.011 | 272 | 757 | 293 | 17845 |
| 05-03-93M | 45 | 97.0 | 5.50 | 1.020 | 357H | 4094 | 128 | 7585 |
| 04-29-93h | 45 | 94.0 | 6.70 | 1.014 | N/T | 1318 | 180 | 10815 |
| 04-22-93h | 45 | 96.0 | 6.80 | 1.020 | 320 | 3900 | 335 | 20168 |
| 04-12-93M | 45 | 94.0 | 7.20 | 1.009 | 260 | 915 | 310 | 18777 |

TABLE 2-continued

| Date | Dose | Temp | pH | SG | CR | u | p | nu |
|---|---|---|---|---|---|---|---|---|
| | | | Mean: | | 285 | 1713 | 297 | 17936 |
| | | | SD: | | 32 | 1146 | 116 | 7042 |
| | | | CV: | | 11.3 | 66.8 | 39 | 39.2 |
| | | | Tests: | | 11 | 12 | 12 | 12 |

Case #2: A.N. is a 44 year old woman whose migraine with aura began approximately 20 years ago. Beginning with blurred vision, subsequent unilateral headaches are invariably accompanied by nausea and vomiting, photophobia, and hypersensitivity to motion of her head and to cigarette smoke. Despite trials of biofeedback, physical therapy, and medications (trials of beta blockers, calcium channel blockers, ergot alkaloids over the years) and drug holidays; the frequency of her headaches has increased over the years to nearly daily occurrence. Lumbar punctures and multiple CT and MRI scans of her head were normal.

Following failure of self-administered IM administration of nalbuphine to control her pain, she began methadone maintenance 24 months ago. Because of many years of prior use of barbiturate-containing compounds her hepatic metabolic function was significantly enhanced requiring more than normal amounts of methadone—as shown by urine plasma concentration estimates. After stabilization on 130 mg per day of methadone, her migraines ceased completely at a plasma methadone level above 135 ng/ml. She continues to experience infrequent stress-related headaches, which are slowly decreasing in severity and frequency.

Urine histories are shown for this patient in Tables 3 and 4. Notice how plasma methadone levels have increased in this patient over time as hepatic function returned to normal by discontinuing barbiturate-containing compounds (bar).

TABLE 3

| Date | Dose | Temp | pH | SG | CR | bar | u | p | nu |
|---|---|---|---|---|---|---|---|---|---|
| 06-01-91S | 100 | N/T | 5.10 | 1.021 | 200 | HI | 6338 | 127 | 3243 |
| 05-29-91W | 100 | N/T | 5.40 | 1.021 | 184 | 2370 | 1985 | 52 | 1339 |
| 05-25-91S | 100 | N/T | 5.40 | 1.020 | N/T | N/T | 1360 | 39 | 995 |
| 05-22-91W | 100 | N/T | 5.10 | 1.013 | N/T | N/T | 1511 | 62 | 1582 |
| 05-20-91M | 100 | N/T | 5.10 | 1.005 | 134 | HI | 615 | 80 | 2026 |
| 05-18-91S | 100 | N/T | 5.40 | 1.017 | N/T | N/T | 2067 | 76 | 1952 |
| 05-15-91W | 80 | N/T | 5.40 | 1.019 | 129 | HI | 1120 | 35 | 1070 |
| 05-13-91M | 65 | N/T | 5.70 | 1.009 | 72 | HI | 335 | 37 | 1367 |
| 05-11-91S | 65 | N/T | 5.10 | 1.016 | 182 | HI | 816 | 25 | 911 |
| 05-08-91W | 50 | N/T | 5.40 | 1.010 | N/T | N/T | 853 | 65 | 2924 |
| 05-06-91M | 40 | N/T | 5.40 | 1.019 | N/T | N/T | 174 | 5 | LOW |
| 05-03-91F | 40 | N/T | 5.40 | 1.009 | 89 | HI | 296 | 26 | 1389 |
| | | | Mean: | | 141 | | 1456 | 52 | 1591 |
| | | | SD: | | 49 | | 1661 | 32 | 840 |
| | | | CV: | | 35.0 | | 114 | 62.3 | 52.7 |
| | | | Tests: | | 12 | | 12 | 12 | 12 |

TABLE 4

| Date | Dose | Temp | pH | SG | CR | bar | u | p | nu |
|---|---|---|---|---|---|---|---|---|---|
| 04-04-92S | 130 | 95.0 | 5.80 | 1.013 | 196 | 0 | 4915 | 373 | 7728 |
| 03-28-92S | 130 | 98.0 | 5.90 | 1.020 | 210 | 0 | 6565 | 287 | 5944 |
| 03-21-92S | 110 | 95.0 | 5.50 | 1.021 | 216 | 0 | 9651 | 278 | 6580 |
| 03-14-92S | 110 | 97.0 | 5.70 | 1.022 | 210 | 0 | 8964 | 282 | 6703 |
| 03-07-92S | 110 | 96.0 | 6.30 | 1.014 | 186 | 0 | 4471 | 455 | 10880 |
| 03-02-92M | 110 | 95.0 | 5.60 | 1.022 | 206 | 0 | 8778 | 254 | 6025 |
| 02-21-92F | 120 | 96.0 | 6.20 | 1.016 | 181 | 0 | 5169 | 403 | 8970 |
| 02-15-92S | 120 | 98.0 | 5.90 | 1.015 | 187 | 0 | 4525 | 306 | 6778 |

TABLE 4-continued

| Date | Dose | Temp | pH | SG | CR | bar | u | p | nu |
|---|---|---|---|---|---|---|---|---|---|
| 02-08-92S | 120 | 96.0 | 6.10 | 1.017 | 181 | 0 | 5506 | 364 | 8074 |
| 01-31-92F | 120 | 95.0 | 6.20 | 1.016 | 218 | 0 | 6896 | 538 | 11966 |
| 01-18-92S | 120 | 96.0 | 5.50 | 1.021 | 224 | 0 | 9503 | 274 | 6031 |
| 01-11-92S | 130 | 96.0 | 5.30 | 1.020 | 182 | 0 | 9494 | 249 | 5117 |
| | | | | Mean: | 206 | 0 | 7036 | 399 | 7566 |
| | | | | SD: | 16 | 0 | 2114 | 90 | 2095 |
| | | | | CV: | 8.0 | 0 | 30 | 26.5 | 27.6 |
| | | | | Tests: | 12 | 12 | 12 | 12 | 12 |

Case #3: Shown in Table 5 are examples of estimated plasma methadone levels for four patients demonstrating how to detect misuse of methadone.

TABLE 5

Utilization of Plasma Methadone Levels
To Uncover Misuse of Methadone
Estimated Plasma Methadone Concentration (ng/ml), p

| Sample | Patient A* | Patient B | Patient C*** | Patient D |
|---|---|---|---|---|
| 1 | 480 | 346 | 89 | 1247**** |
| 2 | 465 | 234 | 44 | 1173**** |
| 3 | 485 | 281 | 50 | 1061**** |
| 4 | 525 | 233 | 334 | 1343**** |
| 5 | 454 | 376 | 84 | 435 |
| 6 | 410 | 208 | 310 | 575 |
| 7 | 531 | 290 | 778 | 427 |
| 8 | 483 | 172** | 800 | 514 |
| 9 | 403 | 0** | 33 | 474 |

*Patient A ingests 90 mg/day of methadone q 24 hr. as instructed. He ingests a does in the clinic on Mon., Wed. and Fri., mean 24-hr. though level is 470 ng/ml with a CV = 9.4%.
**Patient B receives 80 mg/day of methadone. She only gets a take home dose for Sunday. Expected mean value (samples 1–6) is 281 +/– 62 ng/ml. Sample 8 was taken 48 hr. after her last dose providing an estimate of plasma methadone half-life of about 65 hrs.
Sample 9 is an example of substitution on a non-patient urine sample.
***Patient C ingests 50 mg/day in clinic on Mon., Wed. and Fri. Her expected plasma concentration should be about 170 ng/ml. She is likely diverting Tues, Thur. and Sun. take home doses and spiking urines with exogenous methadone on other days. Solution was to withdraw take home doses.

TABLE 5-continued

Utilization of Plasma Methadone Levels
To Uncover Misuse of Methadone
Estimated Plasma Methadone Concentration (ng/ml), p

| Sample | Patient A* | Patient B | Patient C*** | Patient D |
|---|---|---|---|---|

****patient D currently ingests 100 mg/day of methadone (samples 5–9). Previously, he was ingesting over 200 mg/day of methadone via supplementing with illicit methadone (samples 1–4). Solution was to slowly taper him back to 100 mg/day on a daily basis of clinic visits.

Cases #4 and #5

Shown in Tables 6 and 7 are data demonstrating how the statistical program is utilized by the computer to 'flag' a urine methadone value as being outside the acceptable range for the patient. Armed with this data, it is possible for a healthcare provider to speak with the patient about this abnormality before it becomes a continuing problem. Typically, lab errors are ruled out prior to discussion with the patient. Assuming no laboratory explanation is forthcoming, the healthcare provider can consider substitution of urine by the patient (often noted by variation in measured urinary parameters, including normalized creatine); ingestion of methadone on a non-24 hour basis; ingestion of additional and unapproved methadone; selling of take-home methadone doses; taking a medication interfering with the metabolism of methadone and so forth. Having an objective and quantitative methadone history to present to the patient overcomes the natural tendency for many patients to be untruthful.

TABLE 6

| Date | Dose | Temp | pH | SG | CR | u | p | nu | Pred |
|---|---|---|---|---|---|---|---|---|---|
| 09-10-93F | 140 | 95.0 | 7.11 | 1.013 | 307 | 3631 | 727 | 17073 | High |
| 09-08-93W | 140 | 95.0 | 5.19 | 1.025 | 306 | 12847 | 204 | 4686 | |
| 09-02-93h | 140 | 95.0 | 5.49 | 1.023 | 317 | 6345 | 154 | 3555 | |
| 08-30-93M | 140 | 95.0 | 4.68 | 1.023 | 316 | 12629 | 144 | 3269 | |
| 08-26-93h | 140 | 95.0 | 4.91 | 1.020 | 224 | 10227 | 186 | 4251 | |
| 08-23-93M | 120 | 94.0 | 4.91 | 1.025 | 239 | 14105 | 172 | 4466 | |
| 08-20-93F | 120 | 94.0 | 5.78 | 1.028 | 299 | 8194 | 172 | 4511 | |
| 08-17-93T | 120 | 94.0 | 5.31 | 1.026 | 311 | 8814 | 145 | 3768 | |
| 08-13-93F | 120 | 94.0 | 6.18 | 1.013 | 357 | 3101 | 318 | 8401 | |
| 08-10-93T | 120 | 95.0 | 5.81 | 1.021 | 296 | 4634 | 173 | 4550 | |
| 08-06-93F | 120 | 95.0 | 6.69 | 1.019 | 243 | 2923 | 252 | 6696 | |
| 08-03-93T | 120 | 95.0 | 5.53 | 1.024 | 185 | 8645 | 201 | 5264 | |
| | | | | Mean: | 283 | 8008 | 237 | 6874 | |
| | | | | SD: | 49 | 3945 | 162 | 3803 | |
| | | | | CV: | 17.3 | 49.2 | 68.3 | 64.7 | |
| | | | | Tests: | 12 | 12 | 12 | 11 | |

TABLE 7

| Date | Dose | Temp | pH | SG | CR | u | p | nu | Pred |
|---|---|---|---|---|---|---|---|---|---|
| 08-06-93F | 130 | 96.0 | 4.88 | 1.025 | 49L | 4305 | 51 | 1858 | LOW |
| 08-02-93M | 130 | 96.0 | 4.81 | 1.024 | 215 | 13601 | 163 | 5922 | |
| 07-29-93h | 130 | 96.0 | 5.05 | 1.019 | 211 | 11015 | 249 | 9089 | |
| 07-26-93M | 130 | 95.0 | LOW | 1.014 | 214 | 8822 | 163 | 5865 | |
| 07-22-93h | 130 | 96.0 | 4.52 | 1.028 | 42L | 4431 | 29 | 1042 | LOW |
| 07-19-93M | 130 | 95.0 | 4.66 | 1.021 | 258 | 25400 | 333 | 12050 | |
| 07-15-93h | 130 | 96.0 | 5.96 | 1.003 | LOW | 5585 | 2642 | 97615 | HIGH |
| 07-12-93m | 130 | 96.0 | 4.76 | 1.021 | 228 | 14361 | 208 | 7550 | |
| 07-09-93F | 130 | 94.0 | 4.76 | 1.015 | 230 | 10940 | 266 | 9663 | |
| 07-06-93T | 130 | 96.0 | 5.20 | 1.024 | 249 | 17816 | 309 | 11313 | |
| 07-01-93h | 130 | 96.0 | 5.10 | 1.012 | 224 | 6963 | 319 | 11630 | |
| 06-28-93M | 130 | 97.0 | LOW | 1.011 | 241 | 7478 | 190 | 6841 | |
| 06-24-93h | 130 | N/T | LOW | 1.009 | 232 | 6889 | 224 | 8088 | |
| | | | | Mean: | 214 | 10585 | 396 | 14502 | |
| | | | | SD: | 41 | 6037 | 681 | 25203 | |
| | | | | CV: | 19.1 | 57 | 172 | 173.7 | |
| | | | | Tests: | 12 | 13 | 13 | 13 | |

Figure 8:
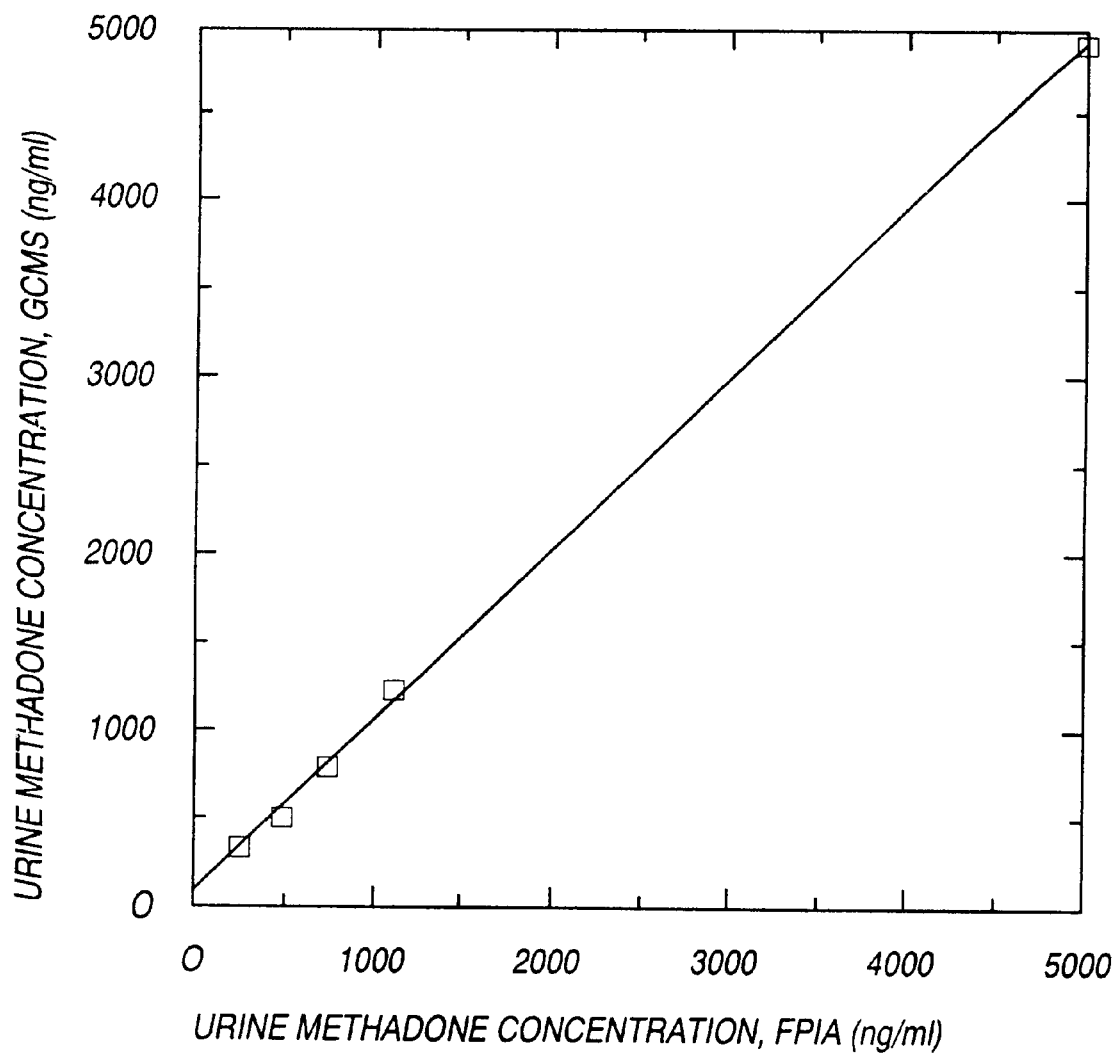
FIG. 8 is a graph of urine methadone concentrations simultaneously measured by FPIA and GC/MS.

Case #6 Methadone concentration data were simultaneously measured using GC/MS and FPIA for urine obtained from five patients and plotted in FIG. 8 for comparison. Linear regression analysis shows that GCMS =0.97FPIA =48, R=0.999: both methods are essentially equivalent. Similarly, methods other than GC/MS or FPIA could also be used, such as gas chromatography, high pressure liquid chromatography, chemical methods and so on, to sequentially follow raw urine methadone concentration patient data for utilization in this invention.

Conclusion

It is thus seen that methods are now provided for monitoring opioids addicted patients who have been placed on methadone maintenance programs for compliance without the need to draw blood for determining plasma methadone concentration. The inventive methods are clinically practical without high laboratory testing cost, the invasiveness of withdrawing blood and the attendant exposure to medical professionals of patient blood having high probability of hepatitis and HIV infection.

While the invention has been described in detail with particular reference to the preferred methods thereof, it should be understood that many modifications, additions and deletions may be made thereto without departure from the spirit and scope of the invention as set forth in the following claims.

What is claimed is:

1. A method of monitoring compliance of a patients that has been placed on a methadone maintenance program which comprises the steps of
   (a) obtaining a sample of the patient's urine,
   (b) measuring the concentration of methadone, the specific gravity and the pH value of the urine sample,
   (c) calculating the concentration of methadone of the plasma as a function of the measured concentration of methadone of the urine, urine specific gravity, and urine pH, and
   (d) comparing the calculated concentration of methadone of the plasma with an expected value for the maintenance program prescribed.

2. The method of claim 1 wherein the urine sample is also tested for adulteration.

3. The method of claim 2 wherein testing for adulteration comprises measuring the creatinine level of the urine sample and comparing the measured creatinine level with a predetermined normal level of creatinine of the patient.

4. The method of claim 1 wherein step (b) the concentration of methadone is measured by fluorescence polarization immunoassay.

5. The method of claim 1 wherein step (c) the concentration of methadone of the plasma is calculated in accordance with the equation $$p = k_1 \cdot u \cdot (k_2 \cdot SGF - k_3)/k_4 \cdot pH^{k_5}$$

where p is the calculated plasma methadone concentration, u is the measured urine methadone concentration, SGF is the specific gravity factor of the patient's urine, pH is the measured pH value of the urine, and $k_1$, $k_2$, $k_3$, $k_4$ and $k_5$ are constants.

6. A method of monitoring compliance of a patient that has been placed on a methadone maintenance program with a prescribed methadone dose which comprises the steps of
   (a) obtaining a sample of the patient's urine,
   (b) measuring the concentration of methadone, the specific gravity and the pH value of the urine sample,
   (c) calculating a normalized urine methadone concentration as a function of the measured urine methadone concentration, prescribed methadone dose, urine specific gravity, and urine pH, and
   (d) comparing the present normalized urine methadone concentration with a previously determined historical base values for the patient's normalized urine methadone concentration to verify compliance;
   whereby if the patient is in compliance with his/her prescribed dose, the present and historical base values of the patient's normalized urine methadone concentration are similar.

7. The method of claim 6 wherein the urine sample is tested for adulteration.

8. The method of claim 7 wherein testing for adulteration comprises measuring the creatinine level of the urine sample and comparing the measured creatinine level with a predetermined normal level of creatinine of the patient.

9. The method of claim 6 wherein step (b) the concentration of methadone is measured by fluorescence polarization immunoassay.

10. The method of claim 6 wherein step (c) the normalized urine methadone concentration is calculated in accordance with the equation:

$$nu=\{(k_1/DOSE)^{k2}\}\cdot\{(k_3/pH)^{-k4}\}\cdot(WGT/k_5)\cdot(k_6\cdot SGF - k_7)\cdot u$$

where nu is the calculated normalized urine methadone concentration, DOSE is the prescribed methadone dose, pH is the pH of the spot urine sample, SGF is the specific gravity factor of the patient's urine, u is the measured urine methadone concentration of the spot urine sample, WGT is the current patient's body weight, and $k_1$–$k_7$ are constants.

11. A method of determining plasma methadone concentration from urine which comprises the steps of
    (a) obtaining a sample of the patient's urine,
    (b) measuring the concentration of methadone, the specific gravity and the pH value of the urine sample, and
    (c) calculating the concentration of methadone of the plasma as a function of the measured concentration of methadone of the urine, urine specific gravity, and urine pH.

12. The method of claim 11 wherein the urine sample is also tested for adulteration.

13. The method of claim 12 wherein testing for adulteration comprises measuring the creatinine level of the urine sample and comparing the measured creatinine level with a predetermined normal level of creatinine of the patient.

14. The method of claim 11 wherein step (b) the concentration of methadone is measured by fluorescence polarization immunoassay.

15. The method of claim 11 wherein step (c) the concentration of methadone of the plasma is calculated in accordance with the equation $$p=k_1\cdot u\cdot(k_2\cdot SGF-k_3)/k_4\cdot pH^{k5}$$

where p is the calculated plasma methadone concentration, u is the measured urine methadone concentration, SGF is the specific gravity factor of the patient's urine, pH is the measured pH value of the urine, and $k_1$, $k_2$, $k_3$, $k_4$ and $k_5$ are constants.

16. The method of claim 6 further comprising the step of measuring the patient's body weight, and wherein calculating the normalized urine methadone concentration also as a function of the measured patient's body weight.

* * * * *